US008667655B2

(12) United States Patent
Campbell et al.

(10) Patent No.: US 8,667,655 B2
(45) Date of Patent: Mar. 11, 2014

(54) APPARATUS FOR ATTACHING A DRIVE SYSTEM AND A STAND TO A RING IN A MEDICINE GANTRY

(75) Inventors: Michael Robert Campbell, South Elgin, IL (US); Jeff Scribner, Glen Ellyn, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 210 days.

(21) Appl. No.: 13/444,881

(22) Filed: Apr. 12, 2012

(65) Prior Publication Data

US 2012/0210571 A1 Aug. 23, 2012

Related U.S. Application Data

(62) Division of application No. 13/101,177, filed on May 5, 2011, now Pat. No. 8,191,222, which is a division of application No. 11/454,757, filed on Jun. 16, 2006, now Pat. No. 7,975,358.

(60) Provisional application No. 60/691,991, filed on Jun. 17, 2005.

(51) Int. Cl.
*B23P 11/00* (2006.01)

(52) U.S. Cl.
USPC .... 29/243.5; 29/266; 29/897.312; 29/898.07; 29/434; 248/125.2; D24/184; 378/195; 378/208; 250/363.05

(58) Field of Classification Search
USPC ............ 29/434, 266, 897.312, 898.07, 243.5; 248/125.2; D24/184; 378/195, 208; 250/363.05
See application file for complete search history.

(56) References Cited

U.S. PATENT DOCUMENTS

| 3,737,660 | A | * | 6/1973 | Ando et al. ...................... 378/39 |
| 4,112,303 | A | * | 9/1978 | Brandt ............................ 378/17 |
| 4,195,227 | A | * | 3/1980 | Carman et al. ............. 250/505.1 |
| 4,592,362 | A | * | 6/1986 | Stedtfeld et al. ................... 5/601 |
| 6,180,943 | B1 | * | 1/2001 | Lange ....................... 250/363.05 |
| 6,412,345 | B1 | * | 7/2002 | Murray et al. ................... 73/468 |
| 2001/0053203 | A1 | * | 12/2001 | Ishii et al. ...................... 378/198 |
| 2002/0168044 | A1 | * | 11/2002 | Tybinkowski et al. ............ 378/4 |
| 2004/0061078 | A1 | * | 4/2004 | Muramatsu et al. ....... 250/492.3 |
| 2004/0170254 | A1 | * | 9/2004 | Gregerson et al. ............ 378/197 |
| 2005/0169621 | A1 | * | 8/2005 | Nomura .......................... 396/72 |

* cited by examiner

*Primary Examiner* — Peter DungBa Vo
*Assistant Examiner* — Jeffrey T Carley
(74) *Attorney, Agent, or Firm* — Peter Kendall

(57) ABSTRACT

An apparatus for securing a drive system to a ring in a medical imaging gantry, the ring defining a central longitudinal axis. The apparatus includes a ring having an outer race and an inner race rotatively mounted within the outer race, the inner race defining inner race teeth about a portion of its circumference, The apparatus also includes a drive system having a drive gear, defining drive gear teeth that are engaged with the inner race teeth, and defining tooth clearance there between. A mounting assembly is also included having at least one mounting bar rigidly attached to the outer race outer facing surface, the mounting bar including a transverse face being substantially perpendicular to the ring outer race circumference, at least one mounting plate secured to the drive system and transverse face of the at least one mounting bar.

6 Claims, 4 Drawing Sheets

APPARATUS FOR ATTACHING A DRIVE SYSTEM AND A STAND TO A RING IN A MEDICINE GANTRY

CROSS-REFERENCE TO RELATED APPLICATIONS

This application claims the benefit of co-pending U.S. patent application entitled "APPARATUS AND METHOD FOR ATTACHING A DRIVE SYSTEM AND A STAND TO A RING IN A MEDICINE GANTRY" filed May 5, 2011 and assigned Ser. No. 13/101,177; which further claimed priority to an application titled, "APPARATUS AND METHOD FOR ATTACHING A DRIVE SYSTEM AND A STAND TO A RING IN A MEDICINE GANTRY" filed Jun. 16, 2006 and assigned Ser. No. 11/454,757 and U.S. provisional patent application filed Jun. 17, 2005 and assigned Ser. No. 60/691,991, the contents of which are incorporated by reference herein.

BACKGROUND OF THE DISCLOSURE

1. Field of the Disclosure

The present disclosure generally relates to nuclear medicine, and more particularly to apparatus and methods for attaching a drive system and a stand to a ring of a medicine gantry in a particular nuclear gantry.

2. Description of the Background Art

Nuclear medicine is a unique medical specialty wherein radiation is used to acquire images that show the function and anatomy of organs, bones or tissues of the body. Radiopharmaceuticals may be introduced into the body, either by injection or ingestion, and are attracted to specific organs, bones or tissues of interest. Such radiopharmaceuticals produce gamma photon emissions which emanate from the body. One or more detector heads are used to detect the emitted gamma photons, and the information collected from the detector head(s) is processed to calculate the position of origin of the emitted photon from the source (i.e., the body organ or tissue under study). The accumulation of a large number of emitted gamma positions allows an image of the organ or tissue under study to be displayed.

There are basically two types of imaging techniques, namely, positron emission tomography (PET) and single photon emission computed tomography (SPECT). Both PET and SPECT require gamma ray detector head(s) that calculate and store both the position of the detected gamma ray and its energy. Typically, detector head(s) include a scintillation plate which converts each received radiation event (e.g., the emitted gamma photons) into a scintillation or flash of light. An array of photomultiplier tubes positioned behind the scintillation plate and associated circuitry determine a coordinate location and a value of energy for each scintillation event. Generally, the detector head(s) is attached to a ring, and a drive system is mounted to a portion of the medicine gantry to rotate the ring.

In a nuclear medicine camera, there are several ways to mount the drive system. One way of mounting the drive system to the gantry is to mount the drive system to the stand to achieve proper tooth alignment (pinion gear centerline is parallel to ring centerline). Here, the stand often has a costly machined surface where the drive system mounts. Even after this surface is machined, the tolerance accumulation between this mounting surface on the stand and gear teeth on the ring may still be large. Furthermore, as the ring and stand both experience unequal deflections under load, the tooth alignment may vary. If the machined surface on the base frame is eliminated for cost reduction purposes, the tolerance accumulation and potential tooth misalignment may further increase.

Adjustable tooth clearance is often used between the pinion gear and ring in a nuclear medicine camera and is accomplished in various ways. One common way is to provide slotted mounting holes in the drive system's mounting plate. During assembly, the mounting plate is slid towards the ring until the desired tooth clearance is achieved bolts are then tightened to secure the connection. Depending on the direction of the slots, the assembler may need to lift some or all of the weight of the drive system to slide it into proper alignment. Additionally, when the drive system is removed, the adjustment procedure must be performed again if the drive system has to be reinstalled, thus resulting in additional process variation.

The ring and stand are generally fastened together at several points to adequately support the heavy loads of the detectors and other system components and also to minimize deflection under these loads. Due to tolerance accumulations and possible slight non-coplanarity of multiple mounting surfaces on the stand, the ring may be rigidly bolted into an overconstrained condition, causing binding of the ring as the ring rotates. If the number of attachment points is reduced, or if some or all of the joints are allowed to be non-rigid, the possibility of binding during rotation of the ring may be eliminated, but the system may also experience more deflection under load.

An apparatus and method of attaching the drive system to the ring with relative ease, accuracy and repetition is lacking in the field. Further, an apparatus and method of attaching the stand of a medicine gantry to its ring while allowing for tolerance and deflection is also lacking.

SUMMARY OF THE INVENTION

Apparatus and methods for attaching the drive system and stand to a ring in a medicine gantry are disclosed.

An embodiment of an apparatus is disclosed for securing a drive system to a ring in a medical imaging gantry, the ring defining a central longitudinal axis. The apparatus includes a ring having an outer race and an inner race rotatively mounted within the outer race, the inner race defining inner race teeth about a portion of its circumference, The apparatus also includes a drive system having a drive gear, defining drive gear teeth that are engaged with the inner race teeth, and defining tooth clearance there between. A mounting assembly is also included having at least one mounting bar rigidly attached to the outer race outer facing surface, the mounting bar including a transverse face being substantially perpendicular to the ring outer race circumference.

In accordance with an apparatus of the present disclosure, the apparatus further includes at least one mounting plate secured to the drive system and transverse face of the at least one mounting bar, at least one moveable adjuster interposed between the mounting plate and supported on the at least one mounting bar and being moveable with respect thereto; and wherein movement of the adjuster moves the mounting plate and drive assembly relative to the at least one mounting bar and varies the tooth clearance.

BRIEF DESCRIPTION OF THE DRAWINGS

The disclosure will become more clearly understood from the following detailed description in connection with the accompanying drawings, in which.

DETAILED DESCRIPTION

The following description is presented to enable one of ordinary skill in the art to make and use the disclosure and is provided in the context of a patent application and its requirements. Various modifications to the disclosed embodiments will be readily apparent to those skilled in the art and the generic principles herein may be applied to other embodiments. Thus, the present disclosure is not intended to be limited to the embodiment shown but is to be accorded the broadest scope consistent with the principles and features described herein.

Figure 1:
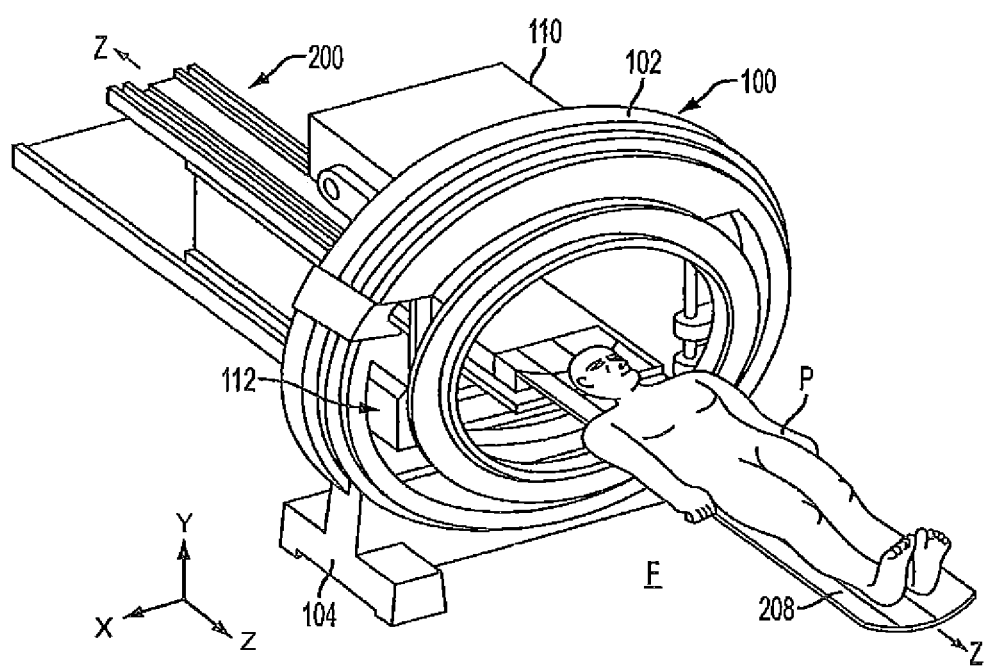
FIG. 1 is a perspective view of a nuclear medicine gantry in accordance with an embodiment of the present disclosure, illustrating the positioning of a patient through the ring of the nuclear medicine gantry.

Referring now to the drawings, and initially to FIG. 1, a nuclear medicine gantry in accordance with the present disclosure is shown and is generally referenced by numeral 100. Nuclear medicine gantry 100 includes a ring 102 operatively connected to and supported on a stand 104. Ring 102 is supported on stand 104 in such a manner that a central longitudinal Z axis of ring 102 is oriented in a plane substantially parallel to floor "F." Ring 102 defines an X-Y plane.

Figure 2:
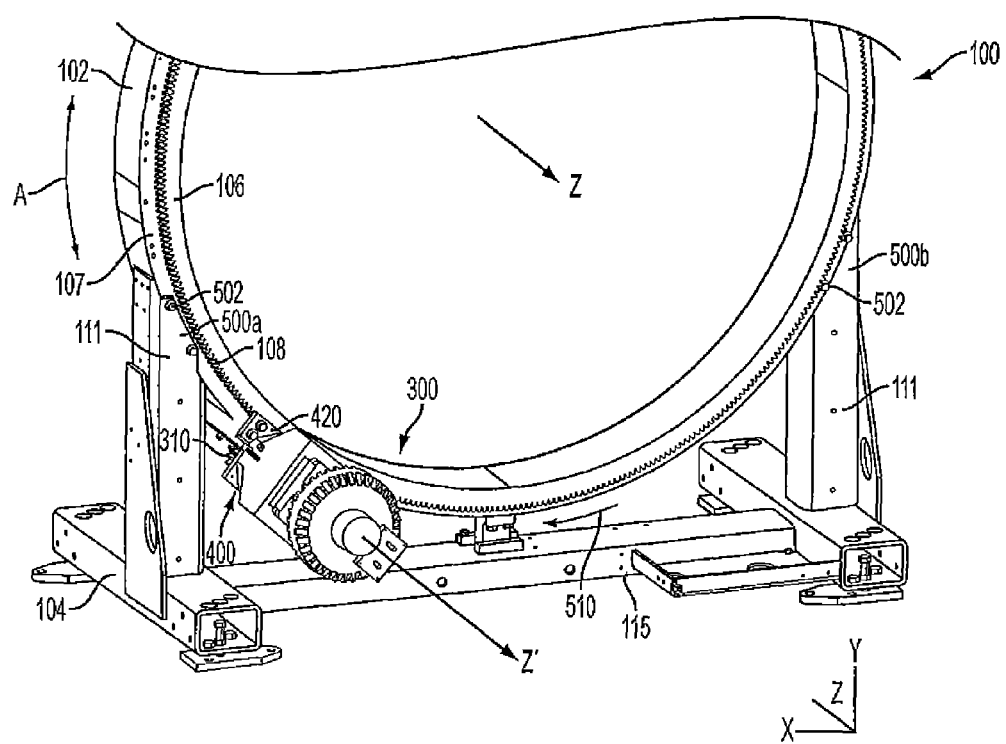
FIG. 2 is a partial perspective view of a ring of the nuclear medicine gantry of FIG. 1, illustrated with a portion of a drive assembly attached thereto.

With reference to FIGS. 1 and 2, ring 102 defines an inner race 106, rotatable about the central longitudinal Z axis, including a series of teeth 108, in the form of a gear, along substantially the entire circumference of inner race 106. Ring 102 also includes an outer race 107, which is shown connected to stand 104. In addition, nuclear medicine gantry 100 may be provided with a drive mechanism 300 attachable to a portion thereof and including a gear 310 having teeth 312, in the form of a pinion, which is configured and dimensioned to engage and cooperate with teeth 108 of gear 102. In this manner, rotation of gear 310 of drive mechanism 300 results in rotation of inner race 106 about the longitudinal Z axis as indicated by double-headed arrow "A" in FIG. 2. While one method of rotating inner race 106 about the longitudinal Z axis has been described, it will be readily apparent to those skilled in the art that other methods of rotating inner race 106 about the longitudinal Z axis can be provided and are intended to be included in the present disclosure.

As seen in FIG. 1, nuclear medicine gantry 100 may further include a first detector head 110 and a second detector head 112, each detector head 110, 112 being operatively associated with and/or mounted to a portion of ring 102. Each detector head 110, 112 is independently translatable in directions radial to the longitudinal Z axis (e.g., radially inward toward the longitudinal Z axis and/or radially outward away from the longitudinal Z axis). For example, depending on the radial orientation of inner race 106 about the longitudinal Z axis, each detector head 110, 112 can be translated, in a radial direction, along at least one of an X axis, a Y axis or an axis oriented at an angle between the X and Y axes (see FIG. 1).

According to the present disclosure and as seen in FIG. 1, a linear telescoping bed may be provided and is shown and generally indicated at 200. Bed 200 is oriented such that a pallet 208 is translatable in directions parallel to the longitudinal Z axis of ring 102. FIG. 1 illustrates a patient "P" lying on pallet 208.

It is contemplated that pallet 208 can be removable and replaced with differing pallets depending on the particular purpose, application and need of the customer. For example, there can be provided a relatively thinner pallet fabricated from aluminum could be used for SPECT and GP (i.e., general purpose) customers wanting low attenuation and close patient proximity; a relatively thicker pallet fabricated from carbon fiber could be used for CT and NM scanning; a scintomammography pallet; a pediatric pallet; a wide whole body pallet with armrests; and/or a cardiac specific pallet.

Details of a nuclear medicine gantry and how it operates are disclosed in U.S. patent application Ser. No. 10/609,738, filed on Jun. 30, 2003, the entire contents of which are hereby incorporated by reference herein.

Figure 3:
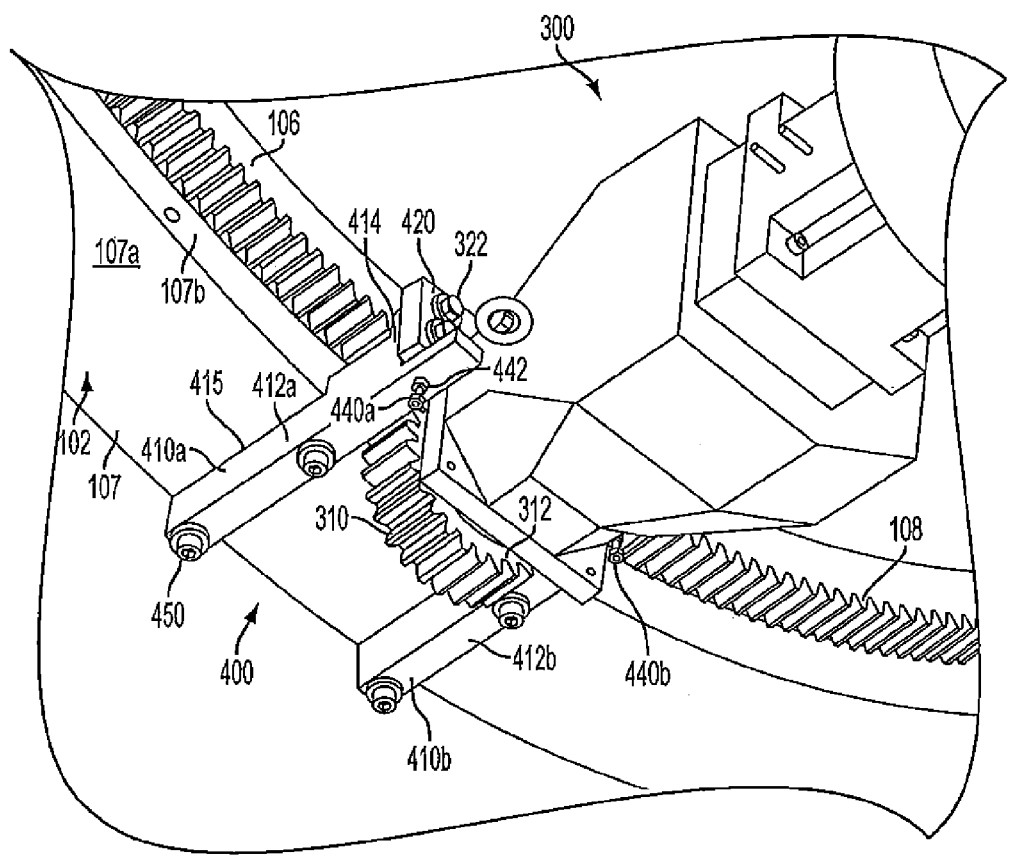
FIG. 3 is an enlarged perspective view of a mounting assembly securing the nuclear medicine gantry of FIGS. 1 and 2 to the drive assembly.

Referring now to FIGS. 2 and 3, a mounting assembly 400 secures and/or aligns driving mechanism 300 with respect to a portion of ring 102. As best seen with reference to FIG. 3, mounting assembly 400 includes at least one mounting bar 410 (two mounting bars 410a, 410b are illustrated), at least one mounting plate 420 (one mounting plate 420 is shown for clarity), and at least one adjuster 440 (two adjusters 440a, 440b are illustrated).

With reference to FIG. 3, each mounting bar 410a, 410b includes a respective base 412 (two bases 412a, 412b are illustrated) and a transverse face 414 (only a single face 414 is illustrated for clarity) and is attached to outer race 107 of ring 102. In the illustrated embodiment, a plurality of bolts 450 affixes base 412 of each mounting bar 410a, 410b to outer race 107 of ring 102. Both mounting bars 410a and 410b are also illustrated substantially parallel to each other and are substantially parallel to central longitudinal Z axis (FIG. 1). Parallelism between each mounting bar 410a, 410b and central longitudinal Z axis may be accomplished by aligning a machined upper surface 415 of mounting bar 410 flush to outside surface 107a of outer race 107.

With continued reference to FIG. 3, each mounting bar 410a, 410b also includes at least one transverse face 414. Transverse face 414 is machined such that transverse face 414 is substantially perpendicular to upper surface 415 of base 412 of each mounting bar 410a, 410b. Additionally, transverse face 414 is substantially parallel to an outer surface 107b of outer race 107. Each mounting plate 420 of mounting assembly 400 is relatively flat and is configured to be removably secured to transverse face 414 of each mounting bar 410a, 410b, possibly via a plurality of bolts 322. Thus, when secured, mounting plate 420 of mounting assembly 400 is substantially perpendicular to outside surface 107a of outer race 107. Furthermore, when secured to transverse face 414 of each mounting bar 410a, 410b, a centerline Z' (FIG. 2) of pinion gear 310 is substantially parallel to central longitudinal axis Z, thus resulting in a desirable tooth alignment between teeth 312 of pinion gear 310 and teeth 108 of gear 102.

Slight adjustments may be necessary after securing drive assembly 300 to ring 102 because the acceptable tooth clearance (typically less than about 0.008 inches) may be smaller than the size and circularity tolerances of ring 102 (typically about 0.015 inches). To make relatively slight adjustments and to improve the alignment of teeth 312 and 108, at least one adjuster 440 may be moved such that it pass through a portion of a respective mounting bar 410a, 410b and contacts a portion of mounting assembly 400 (e.g., a flanged area (not shown) of mounting plate 420).

Adjuster 440 (e.g., a setscrew) may be moved (e.g., turned) in either direction to move mounting assembly 400 towards or away from center of ring 102. Movement of mounting assembly 400 may be facilitated by slots (not explicitly shown) in mounting plate 420 where bolts 322 pass through. During these slight adjustments, the weight of drive assembly 300 is supported by adjuster(s) 440. Once in a desired position, a locking mechanism 442 (e.g., a jam nut) may be used to lock adjuster 440 in place. Once adjuster(s) 440 is locked in place, mounting plate 420 is fixedly secured to a respective mounting bar 410a, 410b (e.g., by tightening bolt(s) 322).

Additionally, this alignment provides a repeatable assembly process. That is, if drive assembly 300 is removed from ring 102 (e.g., to be transported), mounting assembly 400 ensures that drive assembly 300 can be re-secured without any additional adjustments and without losing accuracy. This alignment does not substantially vary when ring 102 is being rotated because inner race 106 and outer race 107 deflect together.

Although not explicitly illustrated in the accompanying figures, apertures, holes, detents or the like may be disposed in various parts to at least partially receive fasteners (e.g., bolts) and/or adjusters 440 (e.g., screws).

Figure 4:
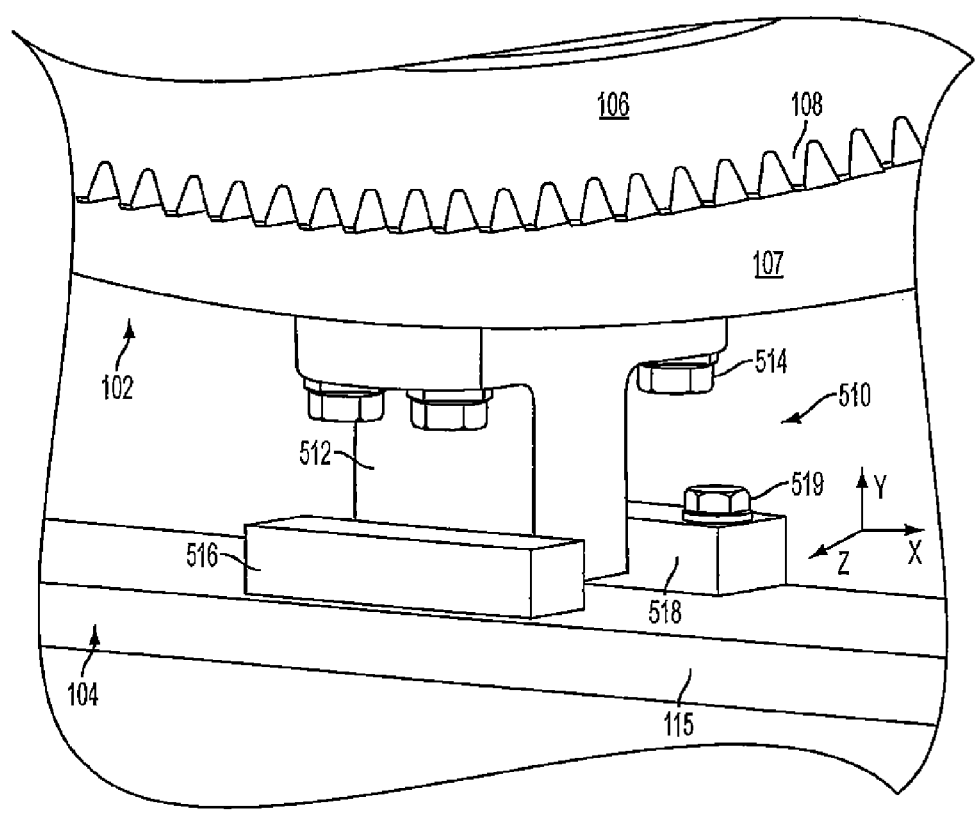
FIG. 4 is an enlarged perspective view of a compliant joint between a portion of a ring and a stand of the nuclear medicine gantry of FIGS. 1-3.

With reference to FIGS. 2 and 4, the present disclosure also relates to a plurality of joints for securing a portion of ring 102 to stand 104 in a nuclear medicine gantry 100. Two rigid connections 500a, 500b and one compliant joint 510 are illustrated in FIG. 2. In the illustrated embodiment, each rigid connection 500a, 500b includes a pair of bolts 502 that secure a leg 111 of stand 104 to a portion of ring 102 (e.g., outer race 107).

Compliant joint 510 is illustrated in FIGS. 2 and 4 near bottom of ring 102 and adjacent crossbar 115 of stand 104. Compliant joint 510 is configured to allow slight motion of a portion of ring 102 (e.g., outer race 107) in the X and Y axes and is configured to substantially prevent motion of a portion of ring 102 (e.g., outer race 107) in the Z axis. In the illustrated embodiment, compliant joint 510 includes a block 512 (a T-shaped block is shown) secured (e.g., via bolts 514) to outer race 107 of ring 102. Compliant joint 510 includes first plate 516 fixedly secured (e.g., welded) to crossbar 115 of stand 104 on one side of block 512, and a second plate 518, is removably secured to crossbar 115 (e.g., via bolt(s) 519). Bolts 514, 519 pass through mounting holes or slots (not explicitly shown) in block 512 and second plate 518, respectfully. It is envisioned that at least one of the mounting holes is slotted to allow the relative position of block 512 and/or second plate 518 to be adjustable along at least the Z axis.

To assemble stand 104 and ring 102, the following steps may be followed:
lower ring 102 onto stand 104 and install bolts 502 at rigid connections 500a, 500b;
slide block 512 into position in contact with first plate 516 and install bolts 514; and
slide second plate 518 into position touching opposite side of block 512 and install bolts 519, such that there is essentially no clearance between block 512 and first plate 516 and second plate 518.

In the described mounting configuration, outer race 107 of ring 102 is supported and resists a cantilevered load caused by detector 110, 112. Additionally, ring 102 is allowed to move slightly in the radial direction (i.e., double-headed arrow "A" of FIG. 2). Such allowance takes the circularity tolerances (about 0.015 inches) of both inner race 106 and outer race 107 of gear 102 into account. Since both races 106, 107 may be slightly egg-shaped, outer race 107 should be able to flex slightly to allow inner race 106 to rotate freely inside without binding. Compliant joint 510 allows such flexing to occur in the radial direction while allowing essentially no motion in the direction (i.e., along the central longitudinal Z axis) that resists the structural load.

Although the present disclosure has been described in accordance with the embodiments shown, one of ordinary skill in the art will readily recognize that there could be variations to the embodiment and these variations would be within the spirit and scope of the present disclosure. For example, it is envisioned to provide a medicine gantry 100 that includes both the described mounting assembly 400 and plurality of joints 500a, 500b and 510, as illustrated in FIG. 2. Accordingly, many modifications may be made by one of ordinary skill in the art without departing from the spirit and scope of the appended claims.

What is claimed is:

1. An apparatus for securing a drive system to a ring in a medical imaging gantry, the ring defining a central longitudinal axis, comprising:
   a ring having an outer race and an inner race rotatively mounted within the outer race, the inner race defining inner race teeth about a portion of its circumference;
   a drive system having a drive gear, defining drive gear teeth that are engaged with the inner race teeth, and defining tooth clearance there between; and
   a mounting assembly, including:
      at least one mounting bar rigidly attached to the outer race outer facing surface, the mounting bar including a transverse face being substantially perpendicular to the ring outer race circumference;
      at least one mounting plate secured to the drive system and transverse face of the at least one mounting bar;
      at least one moveable adjuster interposed between the mounting plate and supported on the at least one mounting bar and being moveable with respect thereto; and
   wherein movement of the adjuster moves the mounting plate and drive assembly relative to the at least one mounting bar and varies the tooth clearance.

2. The apparatus of claim 1, further comprising:
   two substantially parallel mounting bars rigidly attached to the outer race outer facing surface, the mounting bars each including a transverse face being substantially perpendicular to the ring outer race circumference; and
   two mounting plates secured to the drive system, each mounting plate affixed to the transverse face of a respective one of the mounting bars.

3. The apparatus of claim 1, wherein the at least one mounting bar is affixed to a portion of the ring by at least one removable fastener.

4. The apparatus of claim 1, wherein the at least one mounting plate is affixed to the at least one mounting bar by at least one removable fastener.

5. The apparatus of claim 1, wherein the at least one adjuster is a screw.

6. The apparatus of claim 1, further including a locking mechanism for locking the at least one adjuster in a desired position.

* * * * *